United States Patent [19]
Sasaki et al.

[11] Patent Number: 5,479,253
[45] Date of Patent: Dec. 26, 1995

[54] SAMPLE TRANSFERRING METHOD AND APPARATUS FOR FLAME TYPE ATOMIC ABSORPTION SPECTROPHOTOMETRY

[75] Inventors: Kikuo Sasaki, Uji; Akira Honda; Seiji Kojima, both of Otsu, all of Japan

[73] Assignee: Shimadzu Corporation, Japan

[21] Appl. No.: 872,752

[22] Filed: Apr. 24, 1992

[30] Foreign Application Priority Data

Apr. 30, 1991 [JP] Japan .................... 3-128392

[51] Int. Cl.⁶ .................................... G01N 1/10
[52] U.S. Cl. ........................... 356/315; 356/417
[58] Field of Search .............. 356/36, 315, 417

[56] References Cited

U.S. PATENT DOCUMENTS

| | | | |
|---|---|---|---|
| 4,259,291 | 3/1981 | Smythe | 422/82 |
| 4,312,591 | 1/1982 | Tomoff | 356/315 |
| 4,494,871 | 1/1985 | Futekov et al. | 356/315 |

FOREIGN PATENT DOCUMENTS

| | | | |
|---|---|---|---|
| 0351761 | 1/1990 | European Pat. Off. | |
| 2537606 | 4/1976 | Germany | |
| 2507260 | 9/1976 | Germany | |
| 3818058 | 12/1989 | Germany | |
| 127649 | 6/1987 | Japan | 356/315 |

Primary Examiner—F. L. Evans
Attorney, Agent, or Firm—Klima & Hopkins

[57] ABSTRACT

A sample transfer apparatus atomizer connected via tube to a sample receiver for micro-sampling. The sample receiver has a funnel-shaped upward opening and is connected to the tube at the base of the funnel. A control unit controls the apparatus to make sure that the sample injected into the sample receiver will be so positioned in the tube that a quantity of solvent is positioned nearer to the vaporizer than the sample, and preferably another quantity of solvent is positioned nearer to the side of the sample receiver relative to the sample. The presence of solvent in the tube positioned nearer to the vaporizer than the sample delays the sample being sucked by the vaporizer, this preventing interruption of the sample flow in the tube and making the atomic absorption waveform more stable.

19 Claims, 10 Drawing Sheets

SAMPLE TRANSFERRING METHOD AND APPARATUS FOR FLAME TYPE ATOMIC ABSORPTION SPECTROPHOTOMETRY

BACKGROUND OF THE INVENTION

1. Field of the Invention

The present invention relates to a sample setting method and an apparatus for setting the sample into a vaporizer of a premixing chamber and, more particularly, for microsampling method for transferring a minute sample thereinto.

2. Description of the Background Art

When the amount of the sample is small as in the case of a bio-sample, it is difficult to transfer the sample by a continuous suction method for transferring the sample continuously via a tube into a flame type atomic absorption spectrophotometer. In such a case, the sample is transferred by a microsampling method.

Figure 14:
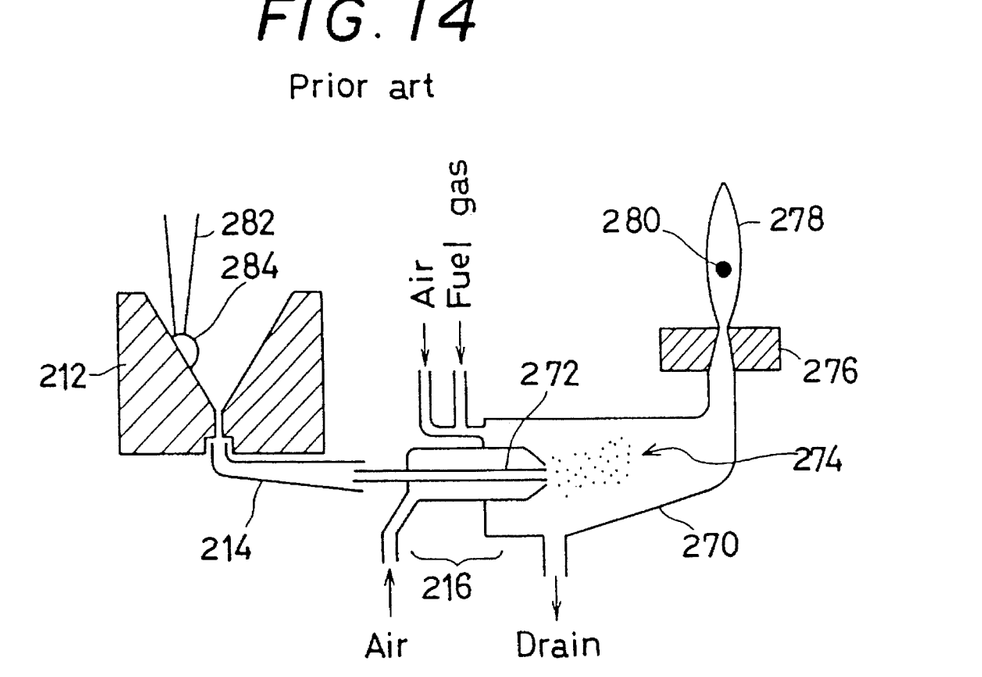
FIG. 14 is a vertical sectional view of a prior art sample transferring apparatus used for a micro-sampling method.

FIG. 14 shows a flame type atomic absorption spectrophotometer provided with an apparatus for transferring the sample by the aforementioned sampling method. The premixing chamber 270 has in its base portion a vaporizer 216 by which the sample injected is vaporized by air supplied from a capillary 272, at the same time a fuel gas and air are mixed with the vaporized sample. The vaporized sample 274 mixed with the fuel gas and air is led to a burner head 276 of the chamber 270 and is atomized in a flame 278. Reference numeral 280 represents an optical axis of an optical flux.

In the microsampling method is used a funnel-shaped sample receiver 212 to facilitate injection of the sample. This sample receiver 212 has an upward opening and a hole at its bottom, and is connected via tube 214 to the capillary 272.

A sample 284 is dripped into the sample receiver 212 by means of a sample injection nozzle 282. When the burner is burning with a flame, the sample supplied to the sample receiver 212 is sucked by negative pressure into the vaporizer 216 and is vaporized before it enters into the burner.

Figure 5A:
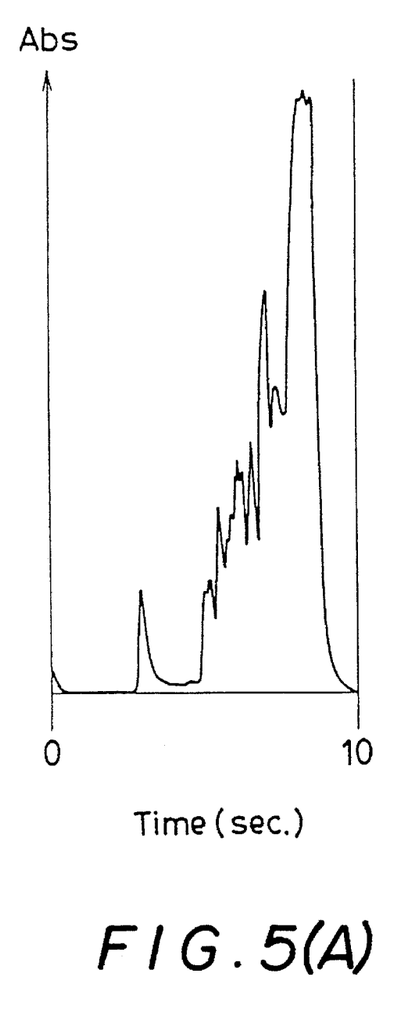
Figure 15:
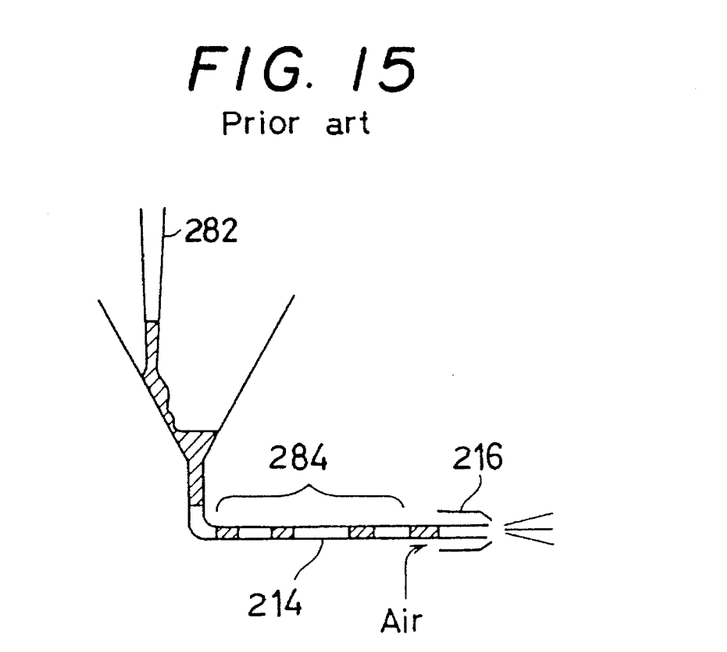
FIG. 15 is a view showing the way a sample is injected by the prior art apparatus.

When in the microsampling method the sample injecting rate into the sample receiver 212 is lower than the suction rate of the vaporizer 216, there results a phenomenon of the supply of the sample 284 being interrupted as shown in FIG. 15. This interruption results in wild fluctuation of the atomic absorption waveform, as shown in FIG. 5 (A), and in the deterioration of the measuring precision.

In case there is a risk of interference caused by coexisting materials in the flame type atomic absorption analysis, it is often possible to reduce measuring errors through matrix modification or by adoption of the so-called standard addition method. In such a case it is necessary to do a pretreatment such as adding a reagent or standard sample to an unknown sample or sometimes to dilute an unknown sample with a blank solution. In a calibration curve method, too, a pretreatment in which the standard sample is diluted stepwise to prepare a series of standard sample solutions diluted generally integer-fold is necessary.

In the flame type atomic absorption analysis method such pretreatment is currently being done by the operator.

Meanwhile, in some types of flameless type atomic absorption spectrophotometer, pretreatment is done automatically by the use of a pretreating apparatus, and solutions to be measured are sucked serially and continuously and are injected at once into a graphite furnace to be atomized. In the flameless type of analysis it is sometimes the case that even if the individual solutions are not thoroughly mixed in the pretreating process such solutions are mixed to some extent by diffusion in the graphite furnace to enable precise analysis. In the flame type of analysis, however, when the solutions sucked serially and continuously by the use of the pretreating apparatus for flameless type analysis are supplied to the vaporizer as they are, the samples are atomized in the order they are supplied, hence there is no meaning of pretreatment.

SUMMARY OF THE INVENTION

An object of the present invention is to obtain a stable atomic absorption waveform through preventing the interruption of the sample flow as the sample is transferred serially in the flame type atomic absorption spectrophotometer by the microsampling method.

Another object of the invention is to automate the pretreating step in the analysis by the use of the flame type atomic absorption spectrophotometer.

According to the present invention, the interruption of the sample flow is prevented through temporary lowering of the rate of sample suction into the vaporizer. Hence, the mode of sample injection or setting is so controlled that the solvent exists in the tube between the sample receiver and the vaporizer at least nearer to the vaporizer than the sample injected into the sample receiver.

An example of the mode of operation according to the present invention will now be described with reference to FIG. 1.

As the sample is sucked into a nozzle 26 of the nozzle mechanism, first the sample (Sam) is sucked upwardly as illustrated in (A), and then the solvent (Sol) is sucked upwardly. It is then preferred to have air (Air) sucked between the sample and the solvent in order to ensure against mixing thereof. When the sample solution is discharged from the nozzle 26 to the sample receiver 12, the solvent is discharged first as illustrated in (B). In the tube 14 the solvent flow may possibly be interrupted by the negative pressure in the vaporizer 16. Then the sample is sucked into the tube 14 as seen from (C), (D). Since the tube 14 is already filled with the solvent as the sample is sucked into the tube 14, this presents a resistance to lower the rate of suction into the vaporizer to ensure against interruption of the sample flow.

Figure 2:
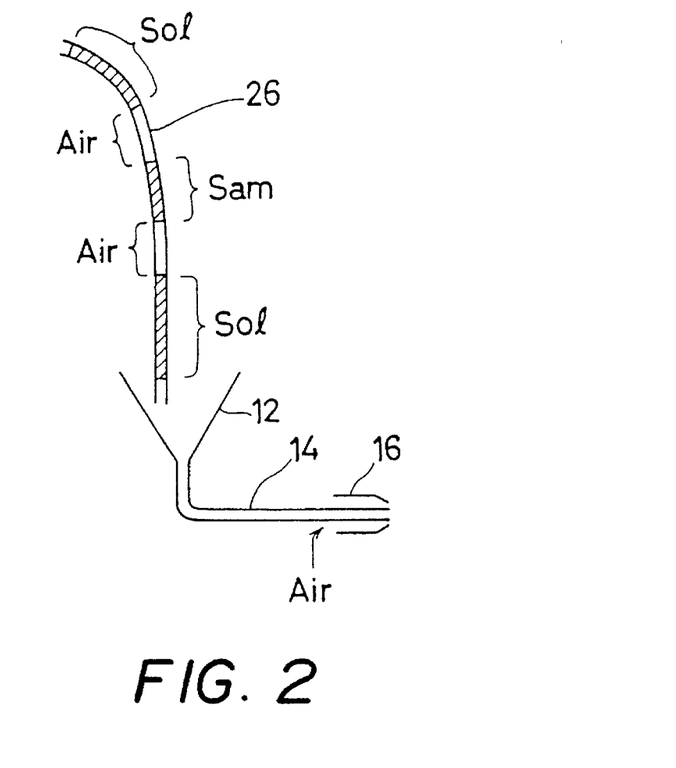
FIG. 2 is a view showing another example of the working principle of the invention.

FIG. 2 shows a condition in which solvent is sucked into the front end and the rear end portion of the nozzle 26 with the sample in between. It is preferred to have air sucked in between the sample and each quantity of the solvent. The sample residue in the sample receiver 12 and the tube 14 is washed off by the solvent discharged later to be cleaned thereby and this also contributes to an improvement of measuring precision since the sample residue, too, can be utilized as supplementary data when the area value of the absorption peak is used.

Figure 3:
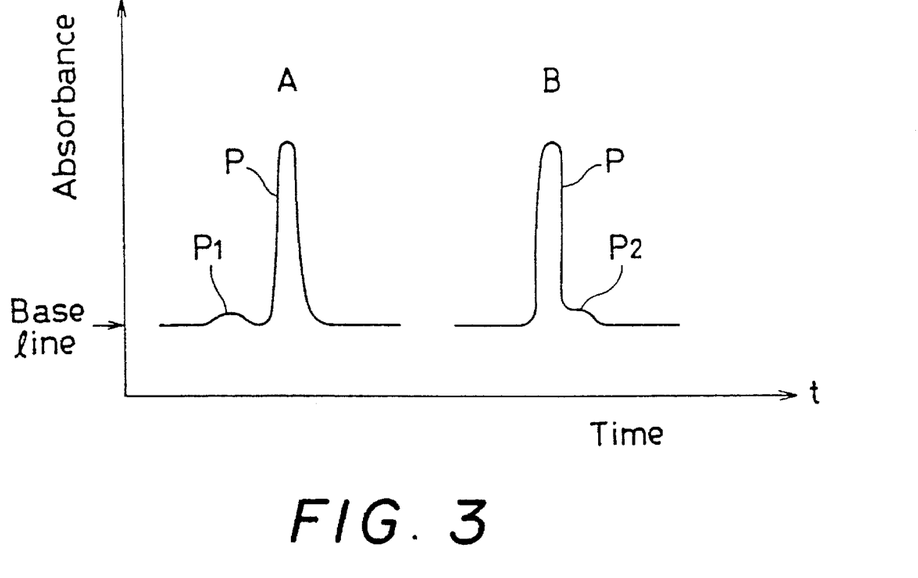
FIG. 3 are waveforms showing atomic spectra obtained by the present invention.
Figure 5B:
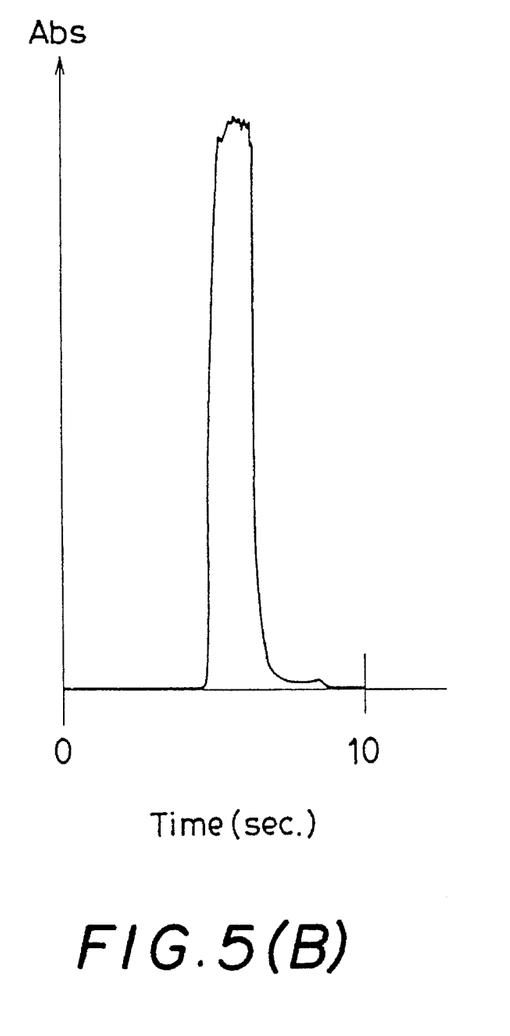

FIG. 3 shows atomic absorption waveforms obtained by the use of the present invention, in which A represents the atomic absorption waveform obtained when the sample is injected by the method illustrated in FIG. 1, and noted is the absorption peak P1 resulting from washing of the sample residue of the previous measurement by the solvent flow before the peak P for the sample in the present measurement. B in FIG. 3 represents the atomic absorption waveform obtained when the sample is injected by the method illustrated in FIG. 2 and noted is the absorption peak P2 resulting from washing of the sample residue of the present measurement by the solvent flow after the peak P for the sample in the present measurement. A specific example of atomic absorption spectroscopy corresponding to B of FIG. 3 is shown in FIG. 5 (B).

According to the present invention, it is so arranged that the solvent is at least nearer to the vaporizer than the sample in the tube connecting the sample receiver with the vaporizer, hence the suction rate of the sample into the vaporizer is lower than in the absence of the solvent to prevent the sample flow from being interrupted in the tube, this resulting in a stable atomic absorption waveform and improved measuring precision.

According to the present invention, the sample pretreating apparatus connected to the flame type atomic absorption spectrophotometer comprises the sample receiver with its bottom connected via a tube with the vaporizer of the atomic absorption spectrophotometer for injecting the sample to the vaporizer, a mixing unit with an outlet in the bottom for discharging liquid residue, a nozzle mechanism having a nozzle for sucking and discharging the sample, and an arm mechanism for moving the nozzle to the necessary position such as a sample supply part for the unknown sample, the standard sample, the reagent or the blank solution etc., the position of the sample receiver and the position of the mixing unit, and is so arranged that the sample mixed in the mixing unit is supplied to the sample receiver.

The nozzle is moved by the arm mechanism to the sample supply part and takes the necessary quantity of the necessary sample such as an unknown sample. The liquids taken are shifted into the mixing unit and there the liquid samples are stirred and mixed by the nozzle's suction and discharge action. After mixing, the mixed sample is taken by the nozzle and then transferred to and discharged into the sample receiver. The liquid sample in the sample receiver is sucked into the vaporizer and then atomized in a flame to be analyzed.

The residual liquid in the mixing unit after taking of the sample is discharged from the bottom of the mixing unit. Then wash liquor is poured into the emptied mixing unit and, washing over, it is discharged from the bottom and the mixing unit, which is then ready for mixing of the next batch.

With this sample pretreating apparatus, dilution of the unknown sample, addition of the standard sample, matrix modification, preparation of a series of diluted solutions of the standard sample, stirring and mixing of the sample solutions, transferring into the vaporizer and taking measurement of the prepared samples, washing of the mixing unit, ect. cetera can proceed automatically according to a pre-programmed process. Hence the work hitherto used to be done manually now proceeds automatically, this resulting in an improvement of efficiency and preclusion of errors due to individual differences in ability by workers.

Also this sample pretreating apparatus is simple in construction since it includes only one mixing unit for mixing a plurality of sample solutions.

The foregoing and other objects, features, aspects and advantages of the present invention will be become more apparent from the following detailed description of the present invention when taken in conjunction with the accompanying drawings.

BRIEF DESCRIPTION OF THE DRAWINGS

FIG. 1 (A)–(D) are views showing one example of the working principle of the present invention.

FIG. 5 (A) and (B) are waveforms showing the atomic absorption spectra obtained by a prior-art method, and that obtained by the use of the apparatus of the present invention shown in FIG. 2 respectively.

FIG. 8 (A) and (B) are views showing a nozzle washer, of which (A) is a plan view and (B) is a vertical sectional view.

FIG. 9 (A) and (B) are views showing a mixing unit, of which (A) is a plan view and (B) is a vertical sectional view of the vessel including aspirator.

DESCRIPTION OF PREFERRED EMBODIMENTS

Figure 4:
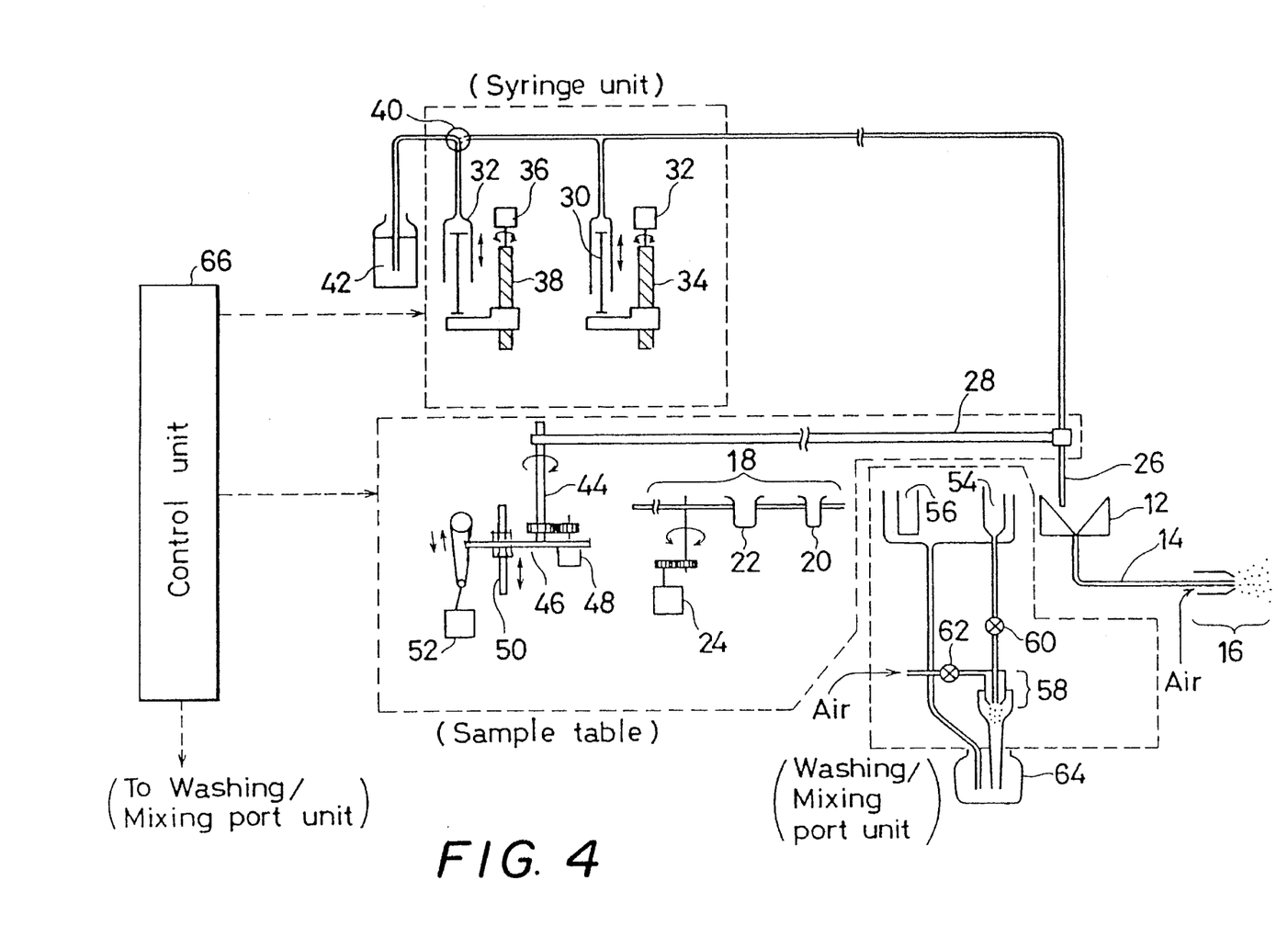
FIG. 4 is a diagram showing an embodiment of the invention.

A preferred embodiment of the invention is shown in FIG. 4.

A vaporizer 16 has connected thereto a sample receiver 12 for microsampling via a tube 14. The sample receiver 12 is funnel-shaped with an upward opening, and the tube 14 is connected to its base. A nozzle 26 of a nozzle mechanism is attached to the tip of a rotary arm 28 in order to inject a sample to the sample receiver 12. The nozzle 26 has connected thereto a syringe unit for discharging the sample taken into the sample receiver 12. Besides a small syringe 30, the syringe unit has connected thereto a large syringe 32 and a container for wash liquor (or blank solution) 42 via a 3-way valve 40. The small syringe 30 is used for sucking and discharging a sample, a reagent or a solvent on a sample table unit or for sucking and discharging the solution mixed by means of a mixing unit 54, while the large syringe 32 is used for stirring to mix a plurality of liquids in the mixing unit 54, for washing the nozzle 26 and the mixing unit 54 and also for supplying the blank solution. For operating the small syringe 30 of the syringe unit there is provided a gear 34 and a motor 32 for driving it, and a motor 36 and a gear 38 for driving the large syringe 32.

The sample table unit has a rotatable shaft 44 rotatably supported on a supporting bed 46 as a mechanism for rotating the rotary arm 28 or moving it vertically, and on the supporting bed 46 there is provided a motor 48 and gears for rotating the rotatable shaft 44. For vertical movement of the supporting bed 46 together with the rotary arm 28, the supporting bed 46, in turn, is supported on a slider 50 to be slidable vertically and the supporting bed 46 is driven vertically, by a motor 52 and a belt mechanism.

The sample table unit has provided thereon a turntable 18 holdings samples and solvents and this turntable has arranged thereon sample cups 20 and reagent bottles 22 containing solvents. The turntable 18 is provided with a motor 24 and a gear mechanism on the rotatable shaft of the turntable 18 for driving it to position a selected sample or solvent to the sampling position.

A washing and mixing port unit is provided for mixing liquids and washing the nozzle after injection of the sample. This unit is provided with the mixing port 54 and a nozzle washing port 56, and a hole in the bottom of the mixing port 54 is connected to aspirator 58 via an on-off valve 60. As compressed air is fed to the aspirator 58 via a valve 62 the residual liquor in the mixing port 54 is sucked by the negative pressure in the aspirator 58 and discharged into a waste bottle 64. It is so arranged that the wash liquor overflowing from the nozzle wash port 56 is discharged into the waste liquor bottle 64.

A control unit 66 controls its subunits or elements which, in turn, control the sample transferring manipulation.

Figure 1A:
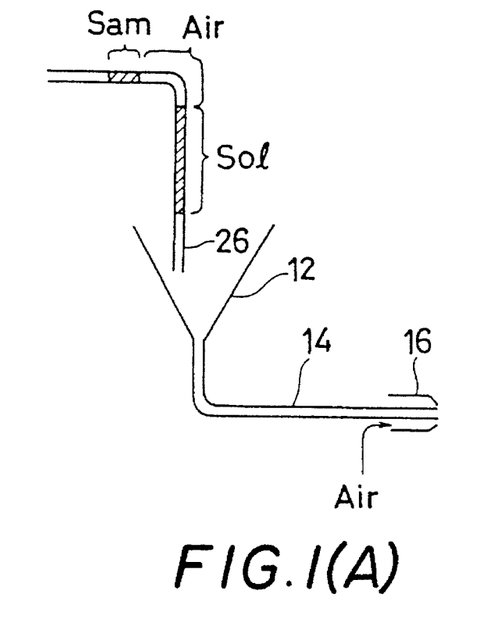
Figure 1B:
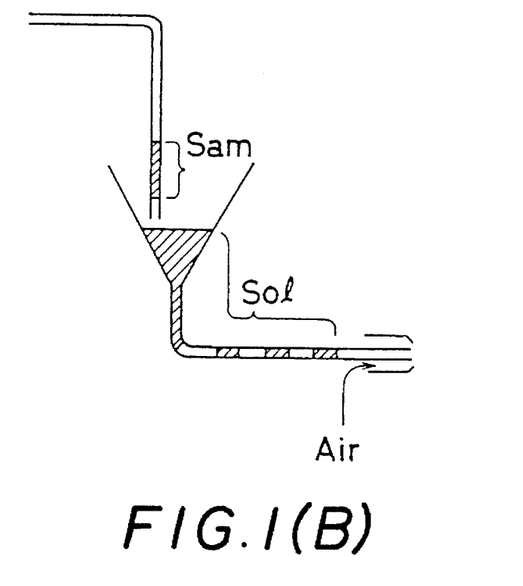
Figure 1C:
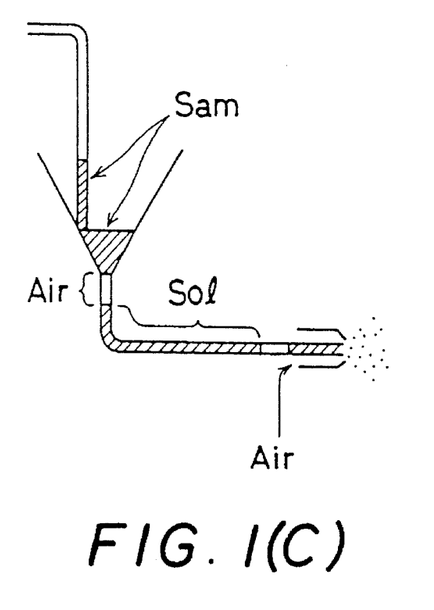
Figure 1D:
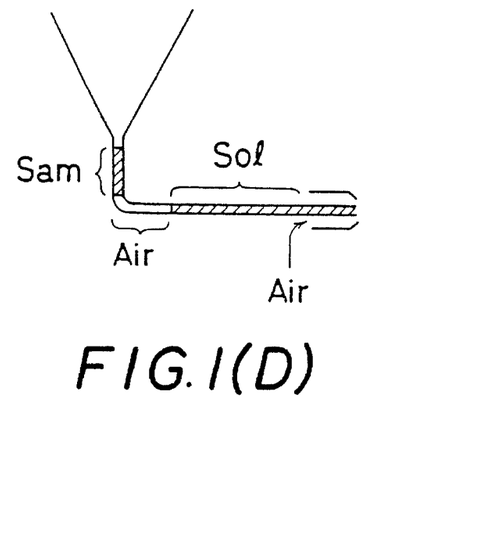

In the embodiment shown in FIG. 4, a the predetermined quantity of the sample itself on the turntable or the sample mixed with reagents or other liquids such as diluting liquid in the mixing port 54 is injected into the sample receiver 12 by the nozzle 26. As seen from FIG. 1 or FIG. 2, the solvent is sucked out of the sample into the tip portion of the nozzle or the sample is sandwiched with the solvent before the sample is injected into the sample receiver 12.

This sample injection procedure is pre-programmed in the control unit 66, and all other units are controlled by the control unit 66 to injet the sample into the sample receiver 12.

As seen from FIG. 4, the mixing port 54 is provided to ensure mixing of the sample without failure. Mixing of the sample, however, may as well be done by using the cups on the turntable 18. Also, washing of the nozzle can be done in the mixing port 54 without using the nozzle washing port 56.

Precluding the interruption of the sample flow is carried out by temporarily lowering the sample suction rate as the sample is sucked from the sample receiver to the vaporizer under negative pressure. For this to occur it is at least necessary to have the solvent sucked into the tip portion of the tube connecting the sample receiver with the vaporizer so as to lower the suction flow rate through the tube. It may as well be possible to connect a 3-way valve amid the tube from the sample receiver to the vaporizer so that normally the solvent only is sucked, and have it switched to the sample receiver side only after an enough quantity of sample has been injected into the sample receiver.

Another sample injection method proposed is to temporarily decrease or stop the supply of air used for sucking and vaporizing the sample when the sample is injected.

When a given sample measurement was taken 10 times by the method illustrated in FIG. 2, the variation in the peak height was 1.33%, while the variation determined by quantitative measurement on the basis of area calculation was 1.44%. In this measurement the nozzle was caused to suck 100 micro-liters of blank solution before and after the sample with air layers of 100 micro-liters in between into the nozzle. Measurement was then taken by injecting the sample into the sample receiver under the above mentioned condition.

Figure 6:
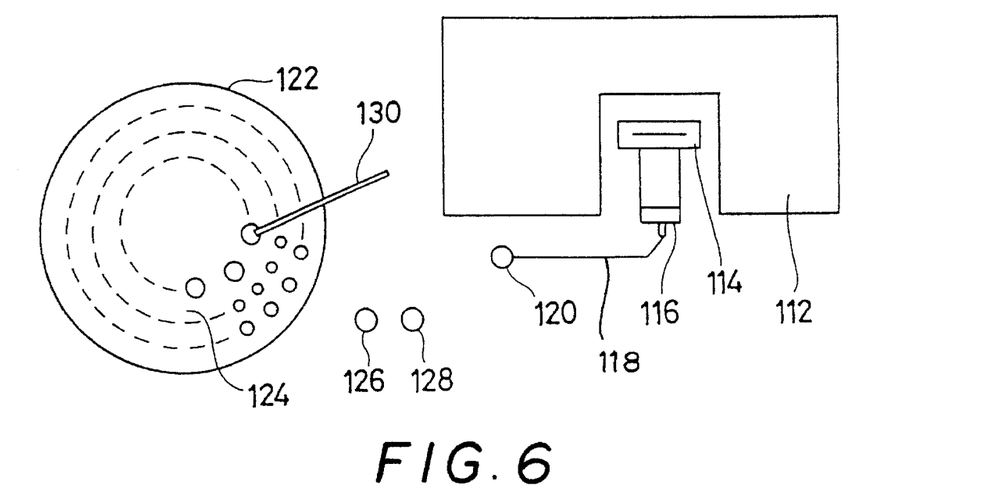
FIG. 6 is a schematic plan view showing a sample pretreating apparatus as an embodiment of the invention.

FIG. 6 shows an embodiment of the sample pretreating apparatus of the invention.

A flame type atomic absorption spectrophotometer 112 with vaporizer 116 and burner 114 is connected with the bottom of a funnel-shaped sample receiver 120 via a polytetrafluoroethylene tube 118. When the burner 114 is burning, the sample solution supplied to the sample injection port 120 is sucked by the vaporizer 116 due to negative pressure, and vaporized therein and transferred to the burner 114.

In the vicinity of the atomic absorption spectrophotometer 112 there is disposed a turntable 122, and on it are arranged containers of unknown samples, standard samples, oil the reagents, blank solutions ect. In the vicinity of the atomic absorption spectrophotometer 112 and turntable 122 there are also disposed a nozzle washer 126 and a mixing unit 128. A sampler arm 130 with a nozzle formed at its tip is provided for moving the nozzle to the positions of the sampling position on the turntable 122, the nozzle washer 126 and the sample receiver 120 to take the required quantities of the sample solution such as an unknown sample and the like arranged on the turntable 122, mix the sample solutions in the mixing unit 128, and inject the sample solution mixed to the sample receiver 120.

Figure 7:
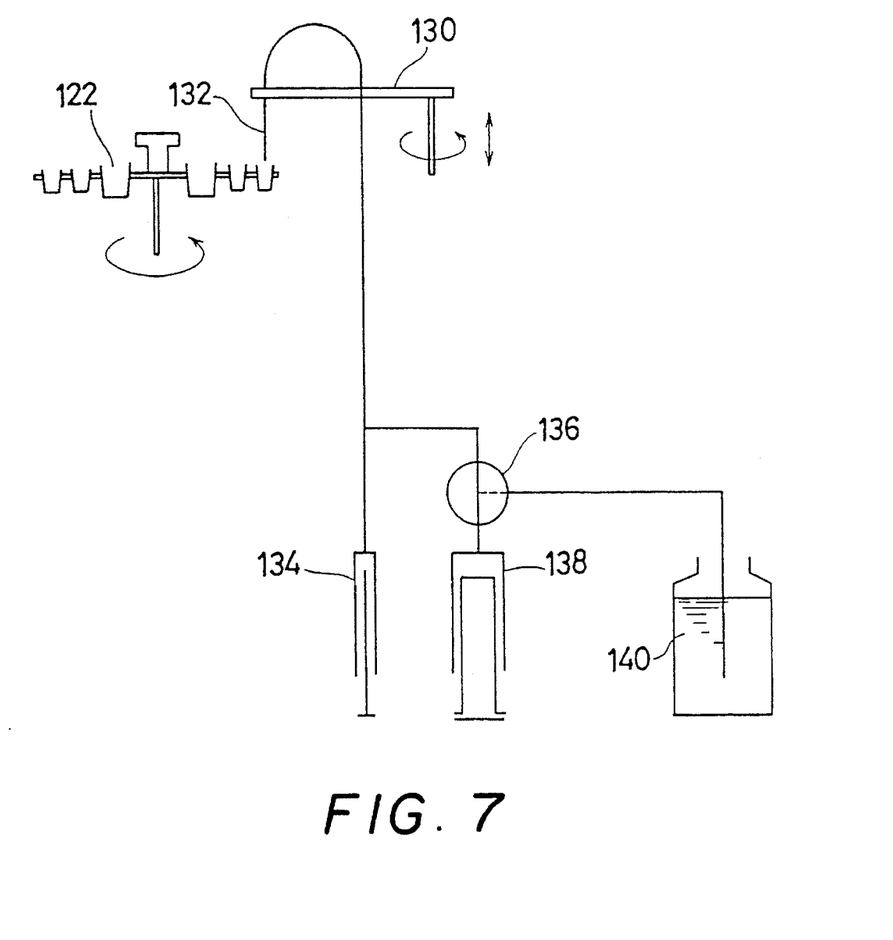
FIG. 7 is a schematic sectional view showing the turntable and suction/discharge mechanism of the pretreating apparatus.

FIG. 7 shows a nozzle mechanism comprising the turntable 122 and the nozzle 132. The nozzle 132 is formed at the front end of the sampler arm 130 and the sampler arm 130 is capable of rotating as well as moving vertically. The nozzle 132 has connected thereto a small syringe 134, and it is also connected with a large syringe 138 and the container for wash liquor (or blank solution) 140 via a 3-way valve 136. The small syringe 134 is used for taking sample solutions arranged in containers on the turntable 122 and also used for taking the solution mixed in a mixing unit 128, and large syringe 138 is used for stirring to mix a plurality of sample solutions in the mixing unit 128, and also used for washing the nozzle 132 and the mixing unit 128 as well as for supplying the blank solution.

Figure 8A:
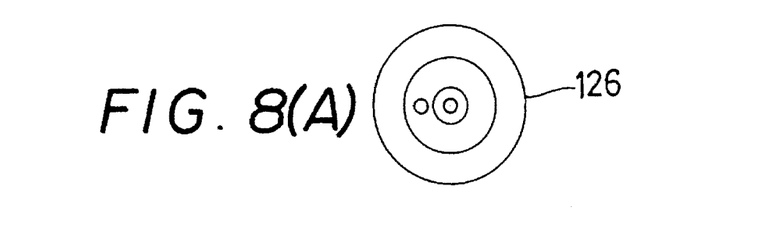
Figure 8B:
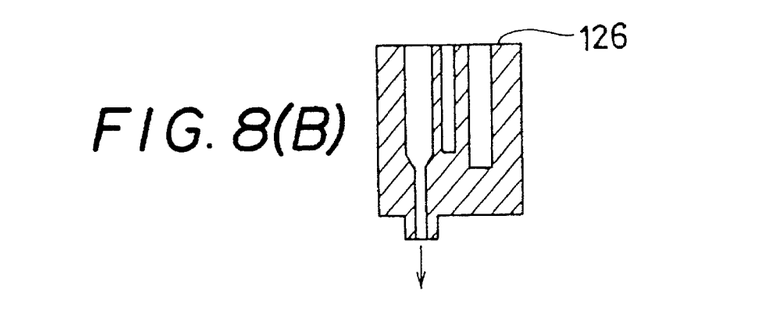

FIG. 8 shows an example of the nozzle washer 126. This nozzle washer 126 is a double-walled round cylinder, the inside wall forming a container in which the nozzle is washed and the outside wall forming a container for discharging the wash liquor having overflowed, and has a hole in the bottom.

Figure 9A:
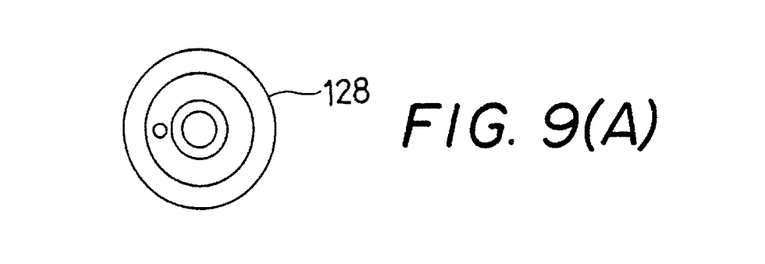
Figure 9B:
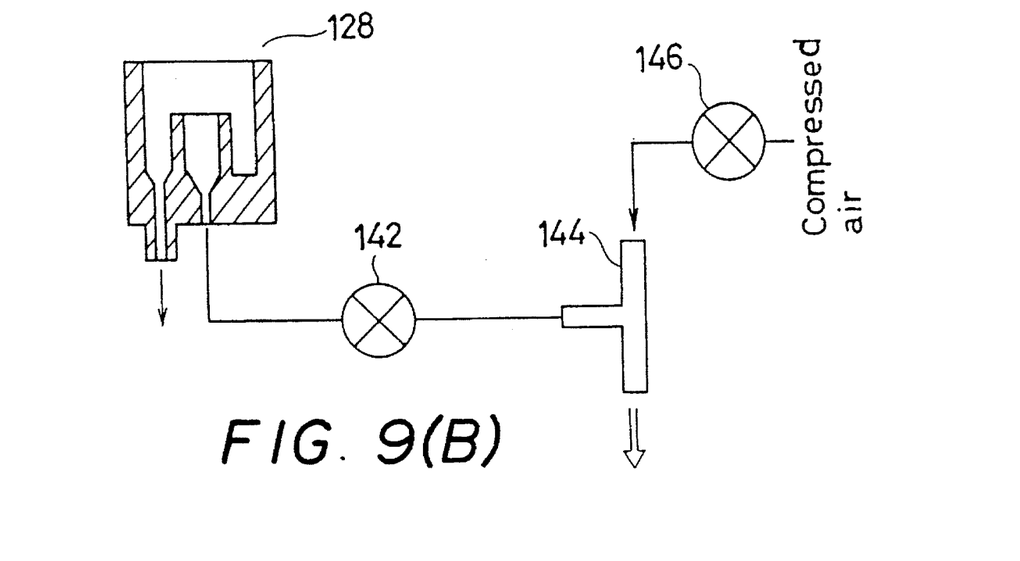

FIG. 9 shows an example of the mixing unit 128. This container 128, too, is double-walled, the inside wall is funnel-shaped, a hole in its bottom is connected to an aspirator 144 via a valve 142, and it is so arranged that the residual liquor in the mixing unit 128 can be removed by suction by the aspirator 144 whose inside pressure is negative, that is, the hole in its bottom is connected to the aspirator 144 via the valve 142, and to this aspirator 144 compressed air is supplied through a valve 146. The outside container of the mixing unit 128 is for discharging the sample solution that has overflowed, and a hole is provided in its bottom.

Figure 10:
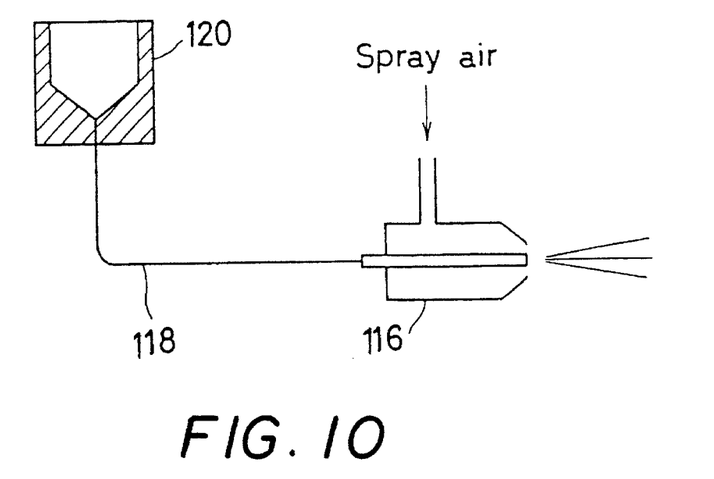
FIG. 10 is a vertical sectional view showing a sample receiver.

FIG. 10 shows an example of the sample receiver 120. This sample receiver 120 is a funnel-shaped container and has its bottom connected to a burner's vaporizer 116 via a polytetrafluoroethylene tube 118. The vaporizer 116 is a sort of nozzle mechanism, arranged to suck the sample solution in the sample receiver 120 by means of negative pressure and vaporize it.

This sample pretreating apparatus, that is, the mode of operation thereof, will be described below with reference to FIGS. 6, 7 and 11, and flow chart of FIG. 12.

The nozzle 132 is moved by the sampler arm 130 onto the turntable 122 and sucks up a blank solution, a reagent, a standard sample and an unknown sample in this order. Then, the sampler arm 130 moves the nozzle 132 to the mixing unit 128 and the sample solutions taken are discharged into the mixing unit 128 by the aid of the small syringe 134. This procedure may be repeated properly depending on the quantity of the sample solution to be taken and the capacity of the small syringe 134. For example, the blank solution alone may first be sucked up to be discharged into the mixing unit 128, then the reagent, the standard sample, and the unknown sample may be sucked up one after another in this order to be discharged into the mixing unit 128.

Figure 11:
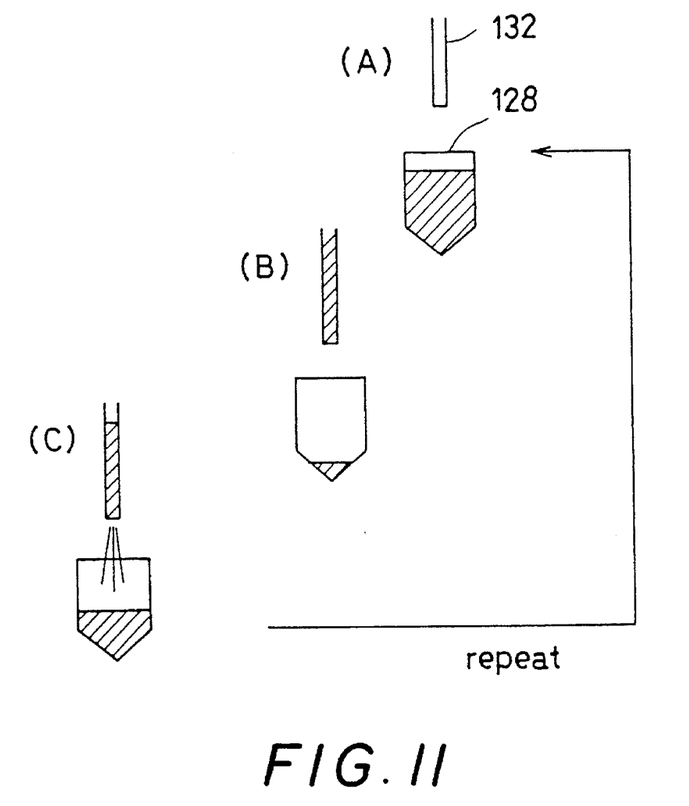
FIG. 11 is a view showing the process of mixing sample solutions in a mixing unit.
Figure 12:
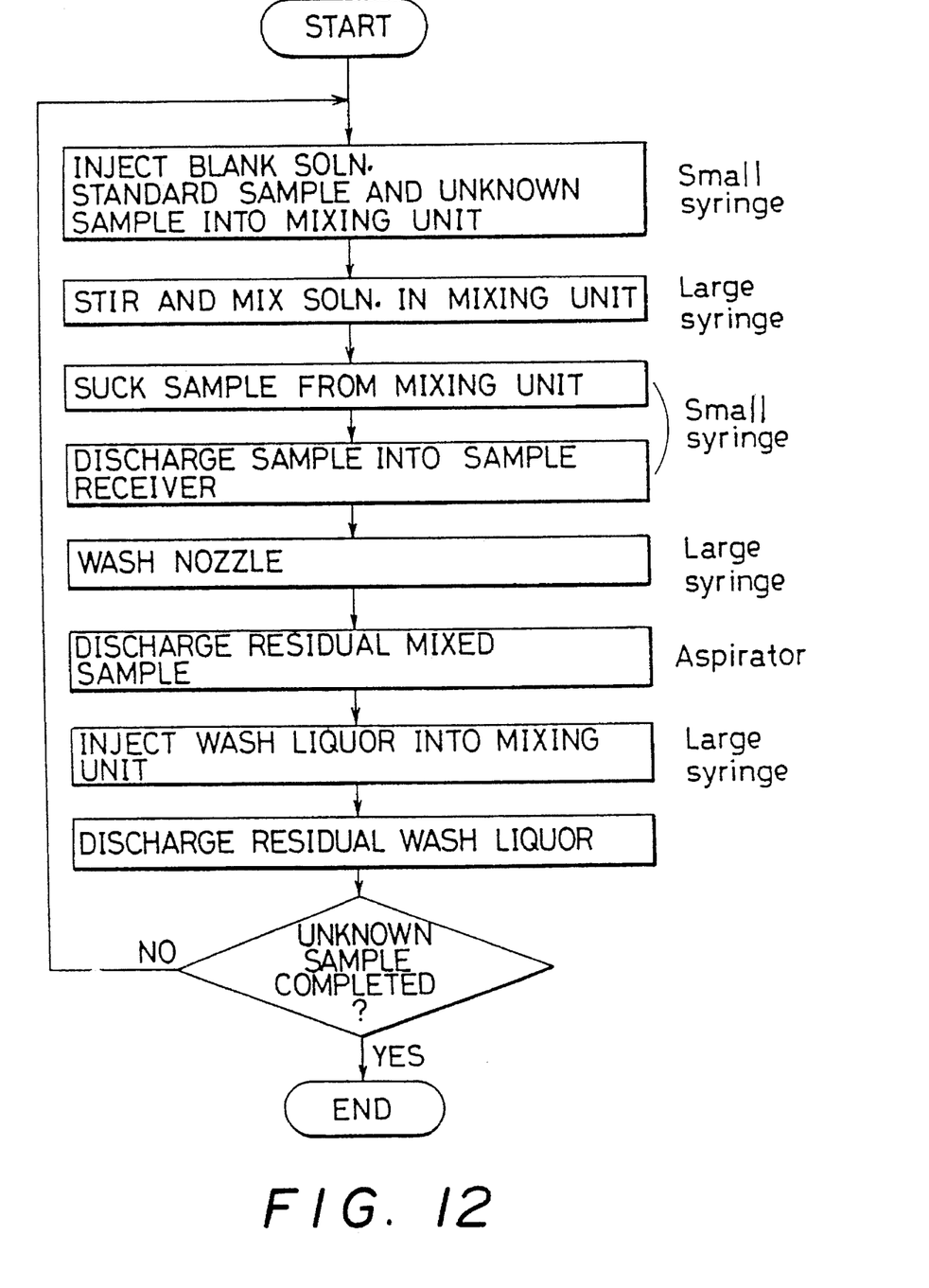
FIG. 12 is a flow chart showing the mode of operation of the sample pretreating apparatus of the present invention.

Then, the 3-way valve 136 is so set that the nozzle 132 is connected to the large syringe 138 and, as shown in FIG. 11, the sample solution discharged into the mixing unit 128 is sucked into the nozzle 132 and is again discharged into the mixing unit 128, and this procedure is repeated until the sample solutions are thoroughly stirred and mixed together. The large syringe 138 is used since it is often the case that the quantity of the sample solution mixed is often in excess of the capacity of the small syringe, and also for increasing the suction and discharge flow velocity to thereby improve the stirring effect.

Then, a part (usually 10–50 micro-liters) of the mixed sample solution in the mixing unit 128 is sucked up by the small syringe 134 and the nozzle 132 moves to the sample receiver 120 to discharge the sucked solution thereinto. If the burner is burning, the sample solution discharged into the sample receiver 120 is sucked and then vaporized by the vaporizer 116, is sent to the burner 114 to be atomized thereby and the atomic absorption analysis done.

Then, the nozzle 132 moves to the nozzle washer 126, the 3-way valve 136 is switched for communication of the nozzle 132 with the container for wash liquor 140, the wash liquor is discharged from the nozzle 132 by the suction and discharge action of the large syringe 138 and the inner and outer surface of the nozzle 132 is washed clean thereby. The wash liquor having overflowed from the nozzle washer 126 is naturally discharged.

Meanwhile, the residue of the mixed sample solution prepared in the mixing unit 128 is vacuum-suctioned and forcibly discharged the outside with the valve 142 opened for compressed air to be delivered to the aspirator 144. The valve 146 is provided to ensure against waste of compressed air, while the valve 142 is for preventing discharge of sample solutions when they are stirred to mix together.

Thereafter, the nozzle 132 moves to the mixing unit 128 and again the wash liquor 140 is injected into the mixing unit 128 by the suction and discharge action of the large syringe 138. It is preferred that the injected quantity of the wash liquor is larger than the capacity of the mixing unit 128. The wash liquor having overflowed from the mixing unit is naturally discharged to the outside. Then, the compressed air is again delivered to the aspirator 144 and the wash liquor in the mixing unit 128 is sucked and forcibly discharged to the outside. Since the wash liquor in the mixing unit 128 is completely discharged by vacuum suction, there is no necessity of drying the mixing unit 128. There is no risk of the phenomenon called "carry over" that affects the result of measurement of the next sample for the mixing unit 128.

Described above is the procedure of taking a single measurement of a singe unknown sample. When it is desired to take measurement of the same sample repeatedly, the same process of pretreating the sample may simply be repeated. If it is desired to take measurement of a plurality of different unknown samples, it is essential to set up a program in advance so that pretreatment of the samples is carried out by the use of different standard samples, reagents and blank solutions, Although in the described embodiments the nozzle washer 126 and the mixing unit 128 are provided separately, it is as well possible to dispense with the nozzle washer whose function can be combined by the mixing unit 128.

Figure 13:
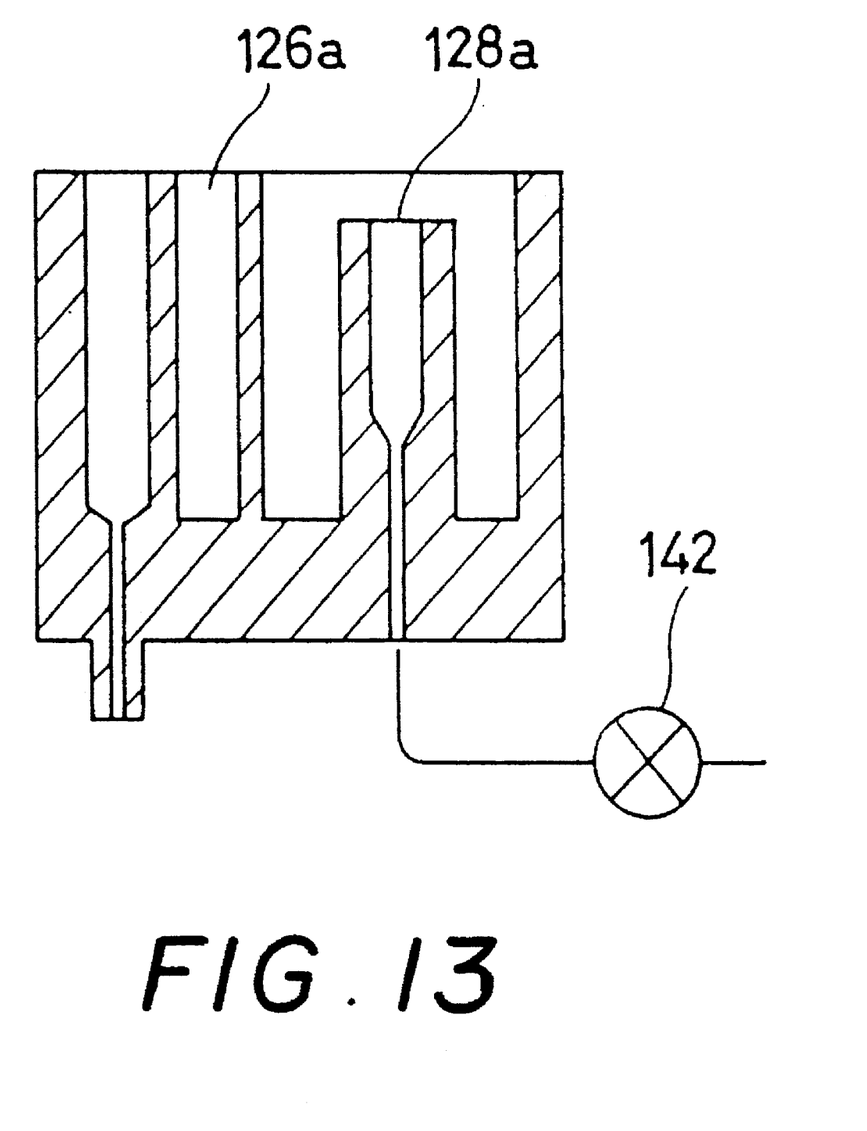
FIG. 13 is a vertical sectional view of an example of integrated nozzle washer and mixing unit.

Also, as shown in FIG. 13, it is as well possible to arrange the mixing unit 128*a* and the nozzle washer 126*a* connected as a single combined unit.

For discharging by sucking the liquid residues in the mixing unit 128, an aspirator is used in the described embodiment, but it is as well possible to use a vacuum pump.

The invention may be embodied in other specific forms without departing from the spirit of essential characteristics thereof. The present embodiments are therefore to be considered in all respects as illustrative and not restrictive, the scope of the invention being indicated by the appended claims rather than by the foregoing description and all changes which come within the meaning and range of equivalence of the claims are therefore intended to be embraced therein.

The features disclosed in the foregoing description in the claims and/or in the accompanying drawings may, both separately and in any combination thereof, be material for realizing the invention in diverse forms thereof.

What is claimed is:

1. A method for injecting a sample into a sample receiver opening, said sample receiver connected via a tube to a vaporizer of a flame atomic absorption spectrophotometer to transfer the sample to the vaporizer, the method comprising the step of:

injecting the sample into the sample receiver in a manner so that solvent exists in said tube at a position nearer to the vaporizer than the sample.

2. A method for injecting a sample according to claim 1, wherein a nozzle is used to take and inject the sample and the solvent, the solvent is sucked after sucking of the sample by the nozzle, and the solvent and the sample are discharged from the nozzle into said sample receiver.

3. A method for injecting a sample according to claim 2, wherein an air layer is sucked between the solvent and the sample in said nozzle.

4. A method for injecting a sample according to claim 2, wherein the solvent also exists nearer to the sample receiver side than the sample in said tube.

5. A method for injecting a sample according to claim 4, wherein the solvent positioned nearer to the atomizer, the sample, and the solvent positioned nearer to the sample receiver are sucked in this order by said nozzle and discharged therefrom into said sample receiver.

6. A method for injecting a sample according to claim 5, wherein air layers are sucked between both solvents and the sample in said nozzle.

7. A method for injecting a sample according to claim 1, wherein there is provided a change-over valve between said sample receiver and said vaporizer, said change-over valve normally causing solvent to be sucked into said vaporizer and, said change-over valve is shifted to said sample receiver side when the sample has been injected into said sample receiver.

8. A method for injecting a sample according to claim 1, wherein the sample injected into said sample receiver is a pretreated sample comprising an unknown sample admixed with at least one of a standard sample, a reagent and a blank solution.

9. A method for injecting a sample according to claim 4, wherein the sample injected into said sample receiver is a pretreated sample comprising an unknown sample admixed with at least one of a standard sample, a reagent and a blank solution.

10. A method for injecting a sample into a sample receiver upwardly opening and with its bottom connected via tube to a vaporizer of a flame atomic absorption spectrophotometer, wherein air supply to said vaporizer is temporarily reduced or stopped when the sample is injected into said sample receiver.

11. A sample transferring apparatus for a flame atomic absorption spectrophotometer, comprising:
   a sample supply unit;
   a sample receiver;
   a tube connected at one end to said sample receiver;
   a vaporizer of the flame atomic absorption spectrophotometer, said vaporizer connected to an opposite end of said tube;
   a nozzle mechanism having a moving mechanism arranged to receive sample by sucking from said sample supply unit and injecting it into said sample receiver; and
   a control unit for controlling the sample injection so that solvent is positioned nearer to the vaporizer than sample in said tube.

12. A sample setting apparatus according to claim 11, wherein said control unit controls the mode of sample injection to ensure the presence of a solvent also nearer to said sample receiver than the sample in said tube.

13. A sample setting apparatus according to claim 11, wherein there is further provided a sample pretreating apparatus, which is provided with a mixing unit being capable of discharging a liquid residue from the bottom, said sample supply unit is provided with at least one of a standard sample, a reagent and a blank solution, besides an unknown sample, said nozzle moving mechanism is so arranged that said nozzle is movable to the necessary position including that of the sample supply unit, of said sample receiver and of said mixing unit and after mixing of the sample in said mixing unit the mixed sample is injected into said sample receiver.

14. A sample setting apparatus according to claim 12, wherein there is further provided a sample pretreating apparatus, which is provided with a mixing unit being capable of discharging a liquid residue from the bottom, said sample supply unit is provided with at least one of a standard sample, a reagent and a blank solution, besides an unknown sample, said nozzle moving mechanism is so arranged that said nozzle is movable to the necessary position including that of the sample supply unit, of said sample receiver and of said mixing unit and after mixing of the sample in said mixing unit the mixed sample is injected into said sample receiver.

15. A method for injecting a sample in a flame atomic absorption spectrophotometer comprising a sample receiver connected to a vaporizer via a tube with a nozzle supplying sample to the sample receiver, comprising the steps of:
   drawing sample into the nozzle;
   drawing solvent into the nozzle after drawing sample into the nozzle;
   injecting the solvent from the nozzle into the sample receiver; and
   injecting the sample from the nozzle into the sample receiver, whereby the solvent moving through the tube prevents interruption of sample flow through the tube.

16. The method according to claim 15, wherein the solvent is injected into the sample receiver in a manner to flow into the tube and reduce the vacuum applied to the sample when it is injected into the sample receiver and flows through the tube.

17. The method according to claim 15, including the step of drawing a quantity of air into the nozzle to separate the solvent and the sample in the nozzle to prevent mixing thereof.

18. The method according to claim 15, including the step of drawing additional solvent into the nozzle after the step of drawing sample into the nozzle.

19. The method according to claim 18, including the steps of drawing quantities of air into the nozzle to separate the sample from the solvents contained in the nozzle to prevent mixing thereof.

* * * * *